United States Patent [19]

Oguro

[11] Patent Number: 5,569,471
[45] Date of Patent: Oct. 29, 1996

[54] MEDICINE FOR THE TREATMENT OF TUMOR

[76] Inventor: Masao Oguro, 48, Ofunekura-machi, Sekiya, Niigata-shi, Japan

[21] Appl. No.: 328,774

[22] Filed: Oct. 28, 1994

[30] Foreign Application Priority Data

Oct. 29, 1993 [JP] Japan .................................. 5-271769

[51] Int. Cl.$^6$ .......................... A61K 33/24; A61K 31/70; A61K 31/505; A61K 31/445
[52] U.S. Cl. ............................ 424/649; 514/34; 514/274; 514/316
[58] Field of Search ............................ 514/316, 34, 274; 424/649

[56] References Cited

PUBLICATIONS

Chemical Abstracts, vol. 116, No. 1, 6 Jan. 1992, Columbus, Ohio, US; abstract No. 118h, "Studies on the metabolic fate of CPT-11 (3). Pharmacokinetics in rats following a single intravenous administration of cpt-11 (PP)." p. 8; * abstract * & Yakubutsu Dotai, vol. 6, No. 1, 1991, pp. 105-125.

Derwent Publications Ltd., London, GB; AN 88-202979 & JP-A-63 141 964 (Koei Chem. Ind. KK.) 1988. * abstract *.

Toxicol. Appl. Pharmacol., vol. 40, No. 1, 1977, pp. 147-159, "T-Lymphocyte depletion and Lesion of choroid plexus and kidney induced by tertiary amines in rats." * p. 148, fig. 1, compound No. 10 * * p. 147 *.

Int. J. Cancer, vol. 50, No. 4, 1992, pp. 604-610, "Effects of CPT-11 in combination with other anti-cancer agents in culture." * p. 606, Left column–paragraph 5 * * p. 606, right column, paragraph 2 *.

*Primary Examiner*—Jerome D. Goldberg
*Attorney, Agent, or Firm*—Oblon, Spivak, McClelland, Maier & Neustadt, P.C.

[57] ABSTRACT

A medicine for the treatment of tumor. The medicine contains 4-piperidino-piperidine or a physiologically acceptable salt thereof as the effective component. Although 4-piperidino-piperidine or a physiologically acceptable salt thereof do not exhibit tumor cell killing effect per se, they suppress propagation of tumor cells, dissolve resistance of other antitumor drugs, and enhance the antitumor activity of antitumor drugs. Therefore, when the medicine according to the present invention is used in combination with other antitumor drugs, their inherent antitumor activity is enhanced. Since the dose of antitumor drugs which are to be used along with the medicine of the present invention can be reduced, adverse side effects are reduced.

6 Claims, 5 Drawing Sheets

MEDICINE FOR THE TREATMENT OF TUMOR

BACKGROUND OF THE INVENTION

1. Field of the Invention

The present invention relates to a medicine for the treatment of tumor, which is useful in the therapy of various cancerous diseases.

2. Description of the Background

Antitumor agents which are used in the treatment of cancerous diseases are generally accompanied by severe adverse side effects, which impose restrictions on the amount of the agents to be dosed. As a result, a problem arises in that expected therapeutic effects cannot be obtained. When a same antitumor drug is repreatedly administered to a patient for a long time, another problem occurs: tumor cells acquire tolerance against the antitumor drug, hindering the expected therapeutic effect from being exhibited. In order to solve these problems, conventional regimens have employed a combined use of plural antitumor agents.

However, the above problems, i.e., restricted dosage, adverse side effects, and drug resistance which are involved in conventional antitumor drugs have not yet been fully solved by the reliance on a combined use of plural antitumor agents.

The inventors of the present invention have investigated the action of wide-range substances and the action exhibited when an antitumor drug is used in combination with another drug, and as a result, have found that 4-piperidino-piperidine or its physiologically acceptable salts can suppress propagation of tumor cells, dissolve resistance against other antitumor drugs, and, when used in combination with other antitumor drugs, can enhance the antitumor effect of such other antitumor drugs.

SUMMARY OF THE INVENTION

Accordingly, an object of the present invention is to provide a medicine for the treatment of tumor, which solves a problem of poor therapeutic effects due to the restricted dosage of a drug for avoiding adverse side effects, as well as resistance acquired by tumor cells occured after a long term dose of a drug.

In one aspect of the present invention, there is provided a medicine for the treatment of tumor which comprises, as its effective component, 4-piperidino-piperidine or a physiologically acceptable salt thereof.

In another aspect of the present invention, there is provided a medicine for the treatment of tumor, in which 4-piperidino-piperidine or a physiologically acceptable salt thereof are used as a tumor cell propagation inhibitor, a resistance dissolving agent for other antitumor drugs, or as an enhancer for enhancing the antitumor activity of antitumor drugs.

In a further aspect of the present invention, there is provided a medicine for the treatment of tumor which comprises, as its effective components, 4-piperidino-piperidine or a physiologically acceptable salt thereof, and one or more antitumor components selected from the group consisting of 5-fluorouracil (5-FU), methotrexate (MTX), cisplatin, adriamycin (ADR), aclacinomycin (ACR), daunomycin (DNR), mitoxantrone, vincristine (VCR), vindesine (VDS) and etoposide.

In a still further aspect of the present invention, there is provided a composition for the treatment of tumor which comprises 4-piperidino-piperidine or a physiologically acceptable salt and a medicinally acceptable carrier therefor.

In a yet further aspect of the present invention, there is provided use of 4-piperidino-piperidine or a physiologically acceptable salt as a medicine for the treatment of tumor.

The above and other objects, features, and advantages of the present invention will be become apparent from the following description.

DESCRIPTION OF THE PREFERRED EMBODIMENTS

Figure 1:
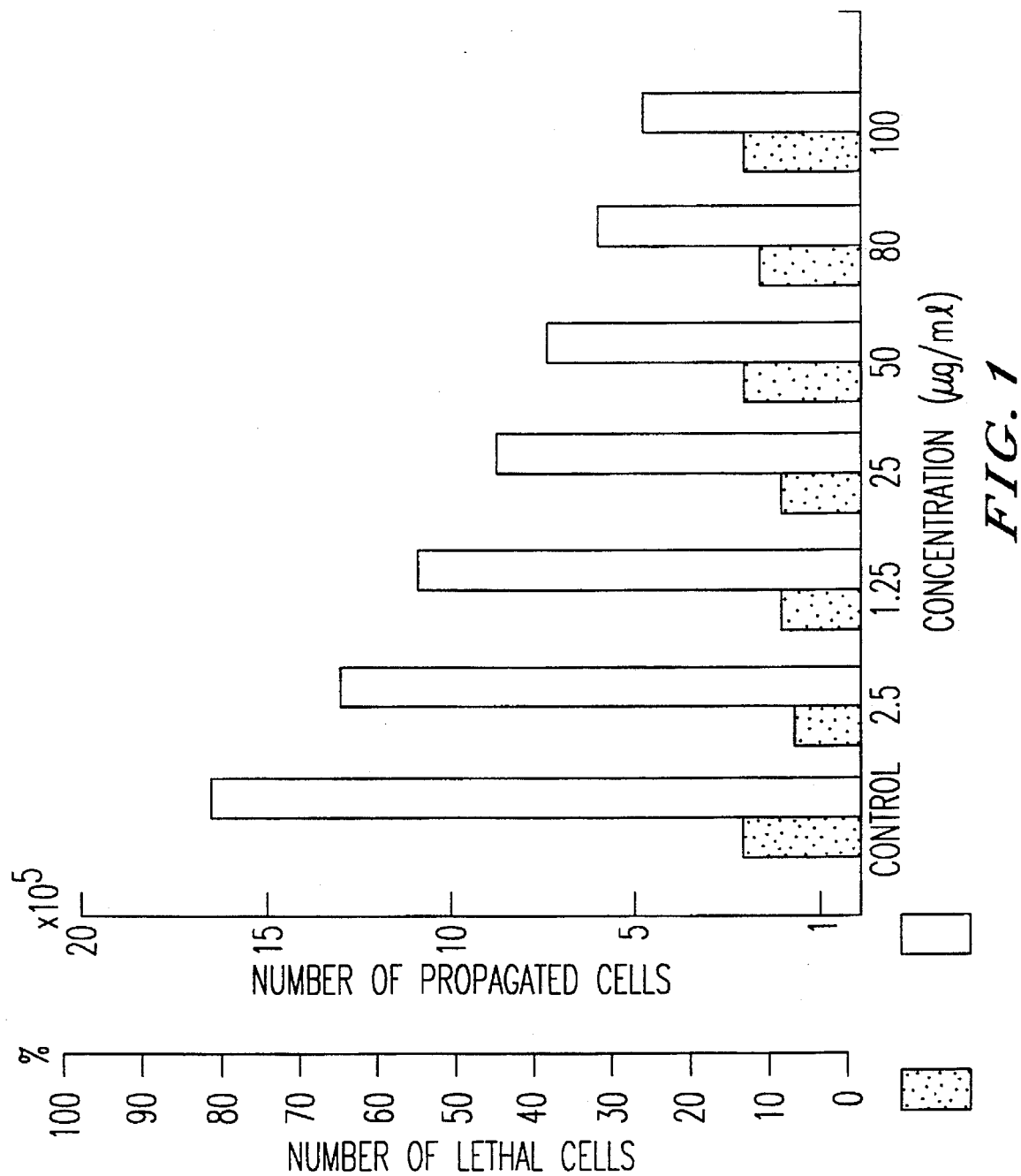
FIG. 1 is a graph which shows the results of a test for confirming a tumor cell propagation inhibitory effect.

The term "medicine for the treatment of tumor" in this invention encompasses not only medicines which exhibit a tumor cell killing effect by themselves, but also those which do not exhibit a tumor cell killing effect by themselves but suppress the propagation of tumor cells or contribute in the treatment of tumor when used in combination with other antitumor drugs, thereby allowing to fully exhibit their own tumor cell killing effects.

The effective component of the medicine for the treatment of tumor according to the invention is 4-piperidino-piperidine. This compound is already known, and is on the market as a reagent for use in various synthetic researches. Physiologically acceptable salts of the compound include acid-addition salts of the compound such as hydrochloric acid salts and nitric acid salts.

Antitumor components which can be used in combination with 4-piperidino-piperidine are not particularly limited. In addition to the antitumor drugs which are presently used, those which are known to exhibit antitumor effects but only insufficiently when used singly, and those which are not suitable for practical use due to their severe adverse side effects can also be used. Specific examples of the antitumor components include pyrimidine antimetabolite such as 5-fluorouracil; folic acid antagonists such as methotrexate; alkylating agents such as nidran; nitrosoureas; mitomycin C; anthracycline antibiotics such as adriamycin; platinum complexes such as cisplatin; alkaloids such as vincristine, and vindesine; topoisomerase-II inhibitors such as aclacinomycin, daunomycin, mitoxantrone, and etoposide; topoisomerase-I inhibitors such as camptothecin, 10-hydroxycamptothecin, 7-ethylcamptothecin, 10-hydroxy-7-ethylcamptothecin, and CPT-11. Among these, 5-fluorouracil, methotrexate, adriamycin, cisplatin, vincristine, vindesine, aclacinomycin, daunomycin, mitoxantrone, and etoposide are preferred. The antitumor components may be used singly or in suitable combination of two or more.

According to the medicine of the present invention, the effective components alone may be used. Alternatively, the effective components may be blended with a medicinally acceptable carrier, and formed into oral or parenteral preparations. Examples of the carrier include binders such as syrup, gum arabic, gelatin, sorbitol, and polyvinylpyrrolidone; vehicles such as lactose, sucrose, corn starch, calcium phosphate, and glycine; lubricants such as magnesium stearate, talc, polyethylene glycol, and silica; disintegrants such as potato starch; and wetting agents such as sodium laurylsulfate, which are all known substances. The medicine of the present invention can take various forms including solid preparations such as tablets, pills, powders, capsules, and granules; liquids; suspensions; emulsions; syrups; elixirs; limonades; topical liquids; injections; intravenous drips; and suppositories.

There is nothing special in the manner of administration when the medicine of the present invention is used in combination with other known antitumor drugs. However, the medicine of the present invention is preferably administered to a patient simultaneously with or prior to the other antitumor drugs.

The dose of the medicine for the treatment of tumor according to the present invention varies depending on the symptom, age, body weight, etc. of the patient. Generally, the medicine of the present invention is administered to a patient in amounts of 1 to 100 mg (as 4-piperidino-piperidine or a physiologically acceptable salt thereof) for each time, one to several times a day, and everyday or every other day while confirming the effect.

EXAMPLES

The present invention will be further described by way of examples, which however should not be construed as limiting the invention.

EXAMPLE 1

Injection preparation

A sterilized hydrochloric acid salt of 4-piperidino-piperidine (100 g) was dissolved in physiological saline for injections to prepare a solution of 10 liters in total. The obtained solution was aseptically charged in ampules (1 ml/ampule), obtaining injection preparations (10 mg/1 vial).

EXAMPLE 2

Tablets for oral administration

| Formulation: | per 1 tablet | charged |
| --- | --- | --- |
| (1) 4-Piperidino-piperidine | 50 mg | 5.0 kg |
| (2) Lactose | 87 | 8.7 |
| (3) Cornstarch | 10 | 1.0 |
| (4) Cornstarch (for glue) | 10 | 1.0 |
| (5) Hydroxypropylcellulose (low substitution degree) | 20 | 2.0 |
| (6) Crystalline cellulose | 20 | 2.0 |
| (7) Magnesium stearate | 3 | 0.3 |

The ingredients (1), (2), (3) and (5) were blended. To the resultant mixture, ingredient (4) was added as a 15% starch glue, followed by granulation. The obtained granules were dried, and then passed through a #16 sieve (nominal size: 1,000 μm) for regulation. The granules which passed through the sieve and ingredient (6) were mixed, and then ingredient (7) was added to the mixture. The resultant mixture was charged in a tableting machine to obtain tablets for oral route each weighing 200 mg and having a diameter of 8 mm.

EXAMPLE 3

Injection preparation containing an antitumor drug

The procedure of Example 1 was followed using a hydrochloric acid salt of 4-piperidino-piperidine (100 g) and vincristine sulfate (10 g, as an antitumor drug), to obtain an injection preparation (10 mg of 4-piperidino-piperidine and 1 mg of vincristine in 1 vial).

EXAMPLE 4

Tablets for oral administration

The procedure of Example 2 was followed except that 4-piperidino-piperidine (5.0 kg), 5-fluorouracil (5.0 kg, as an antitumor drug), and lactose (3.7 kg) were used to obtain tablets for peroral administration.

EXAMPLE 5

Toxicity test

The $LD_{50}$ value of 4-piperidino-piperidine is about 200 to 300 mg/kg. Therefore, ordinary dose will not cause any risk.

EXAMPLE 6

Test for confirming the inhibitory effect on tumor cell propagation

To samples of T-cells derived from human acute leukemia (RPMI-8402, T-ALL cells, see Minowada, J. and Moore, G. E., In Comparative Leukemia Research, Eds. Ito, Y. and Dutcher, R. M., Univ. Tokyo Press, Tokyo, pp. 251–261, 1975), 4-piperidino-piperidine (4-PP) in various concentrations was added (0, 2.5, 12.5, 25, 50, 80 and 100 μg/ml). After a 6-day culture, lethal cells and propagated cells were counted. The results are shown in FIG. 1.

As shown in FIG. 1, the number of lethal cells counted for each dose was not significantly different from the count of the control group. By contrast, the number of propagated cells decreased in a dose-dependent manner. Thus, the effect of inhibiting tumor cell propagation was confirmed.

EXAMPLE 7

Test for confirming the resistance dissolving effect

As drug-fast cells, two kinds of human myeloid leukemia cells (K-562) which had acquired drug resistance against adriamycin (ADR) and cisplatin were used (see Kaoru MIURA, et al., "NK and LAK cell sensitivity and HLA expression" 51st Conference of Japan Cancer Association, page 252, 1992; and Nobutaka IMAIZUMI, Yoichiro KUSUKI, Chie KAWACHI, et al., "Establishing adriamycin-resistant strains and review on the mechanism of resistance", Oncologoa, 21, 89–94, 1988). In the test, adriamycin (ADR), cisplatin, and 4-piperidino-piperidine were dosed singly or in combination against the two kinds of the drug-fast cells, and the number of the lethal cells were counted. The results are shown in FIG. 2.

Figure 2:
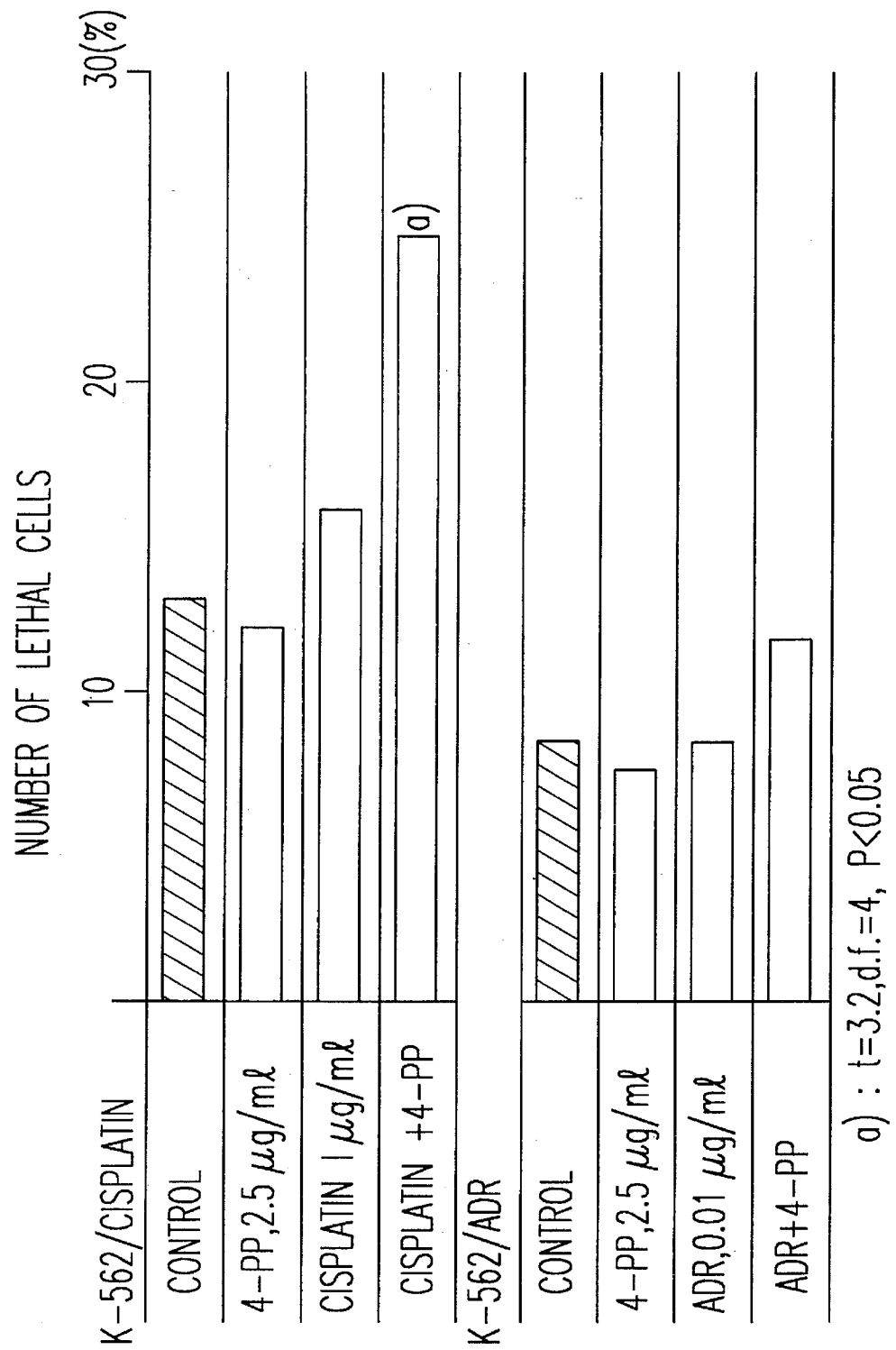
FIG. 2 is a graph which shows the results of a test for confirming a resistance dissolving effect.

As apparent from FIG. 2, on the cisplatin-resistant strains, the 4-piperidino-piperidine single dose group (2.5 μg/ml) and the cisplatin single dose group (1 ηg/ml) exhibited almost the same cell killing effect as that of the control group. When cisplatin and 4-piperidino-piperidine were simultaneously dosed, the cell killing effect was significantly enhanced compared with the case where they are dosed independently and singly, clearly demonstrating the effect of dissolving resistance. The adriamycin-resistant strains also revealed the similar effects of simultaneous administration as demonstrated on cisplatin-resistant strains.

EXAMPLE 8

Test for confirming the effect of enhancing antitumor activity by successive dosage The tumor cell killing effect was investigated by successively administering 4-piperidino-piperidine and an antitumor drug to T-ALL cells.

Figure 3:
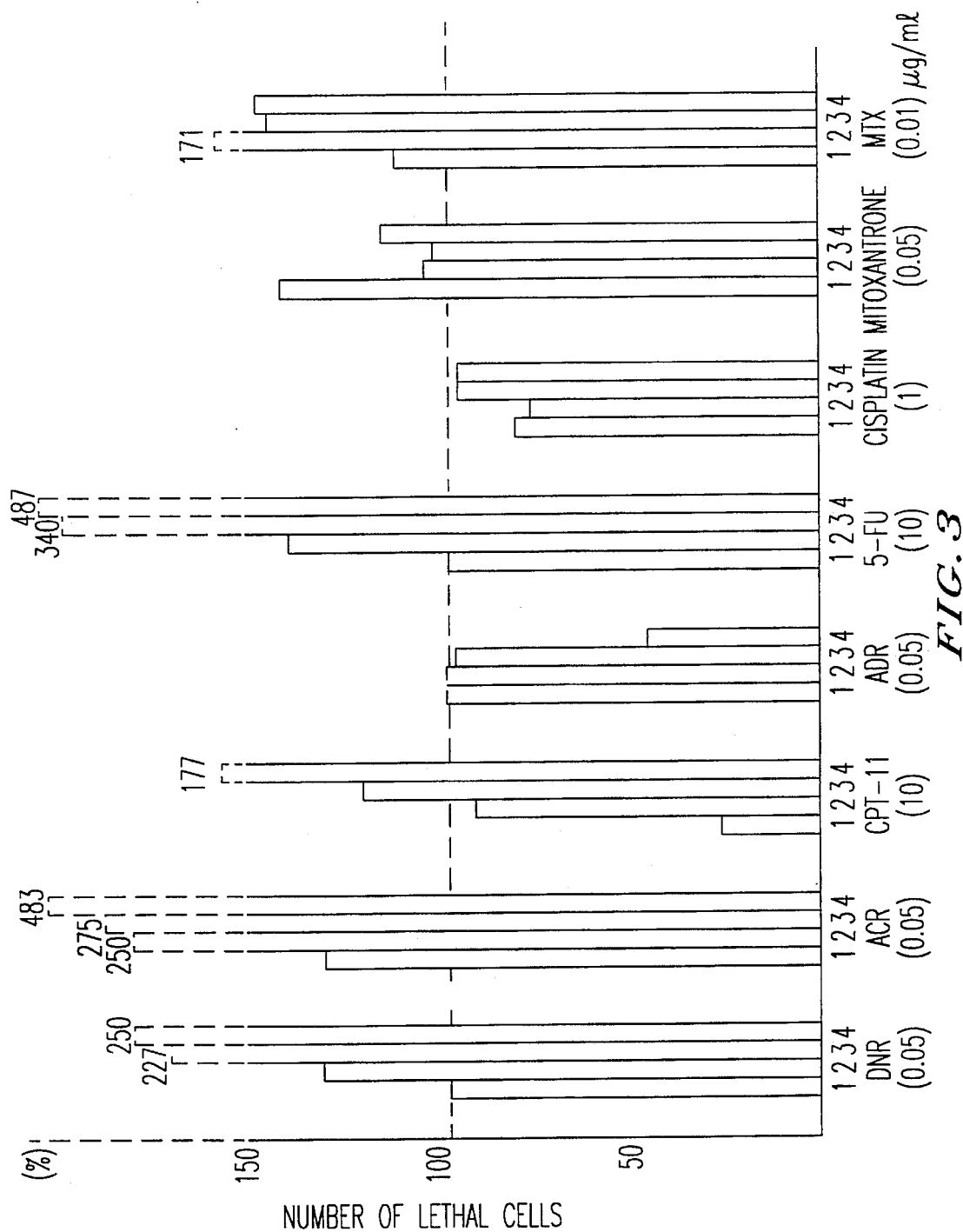
FIG. 3 is a graph which shows the results of a test for confirming an antitumor activity enhancing effect.

First, T-ALL cells were cultured in a plurality of culture media containing 4-piperidino-piperidine at different concentrations (2.5, 12.5, 25 and 50 μg/ml) for 6 days. Eight kinds of the antitumor drugs listed in Table 2 were added to the cells of the groups which were cultured in a normal culture medium for 3 weeks, and also to the cells of the groups which did not contain 4-piperidino-piperidine (standard cells), and the number of the lethal cells was counted. The results are shown in FIG. 3, which employs a relative expression where the number of lethal cells in the standard cell groups was taken as 100% (shown by a horizontal perforated line). The numbers 1, 2, 3 and 4 given for each drug indicate that the concentration of 4-piperidino-piperidine used for the culture is 2.5, 12.5, 25 and 50 μg/ml, respectively.

TABLE 2

| Antitumor drug | Dose (μg/ml) |
| --- | --- |
| Daunomycin (DNR) | 0.05 |
| Aclacinomycin A (ACR) | 0.05 |
| 7-Ethyl-10-piperidino-piperidinocarboxycamptothecin (CPT-11) | 10 |
| Adriamycin (ADR) | 0.05 |
| 5-Fluorouracil (5-FU) | 10 |
| Cisplatin | 1 |
| Mitoxantrone | 0.05 |
| Methotrexate (MTX) | 0.01 |

As apparent from FIG. 3, with respect to CPT-11, the groups where 25 and 50 μg/ml of 4-piperidino-piperidine were precedently dosed revealed that the effect of CPT-11 was enhanced. Similarly, with respect to DNR and 5-FU, the groups where 12.5, 25 and 50 μg/ml of 4-piperidino-piperidine were precedently dosed revealed enhanced effects. ACR and MTX exhibited enhanced effects in all the concentration groups. Mitoxantrone exhibited enhanced effects in the groups where 2.5 and 50 μg/ml of 4-piperidino-piperidine were precedently dosed.

EXAMPLE 9

Test for confirming the effect of enhancing antitumor activity by a simultaneous dosage The numbers of the lethal cells were counted in cases where 4-piperidino-piperidine (2.5 μg/ml) and each of the ten kinds of the antitumor drugs listed in Table 3 were simultaneously dosed (in small amounts and large amounts for each drug), and where the ten kinds of the antitumor drugs were independently and singly dosed (in small amounts and large amounts for each drug). The results are shown in FIG. 4.

TABLE 3

| Antitumor drug | Dose (μg/ml) | |
| --- | --- | --- |
| | S | L |
| Daunomycin (DNR) | 0.01 | 0.05 |
| Aclacinomycin A (ACR) | 0.05 | 0.1 |
| Adriamycin (ADR) | 0.01 | 0.05 |
| 5-Fluorouracil (5-FU) | 5 | 10 |
| Cisplatin | 1 | 5 |
| Mitoxantrone | 0.05 | 0.1 |
| Methotrexate (MTX) | 0.01 | 0.05 |
| Vincristine (VCR) | 0.01 | 0.05 |
| Vindesine (VDS) | 0.01 | 0.05 |
| Etoposide | 0.5 | 1 |

Figure 4:
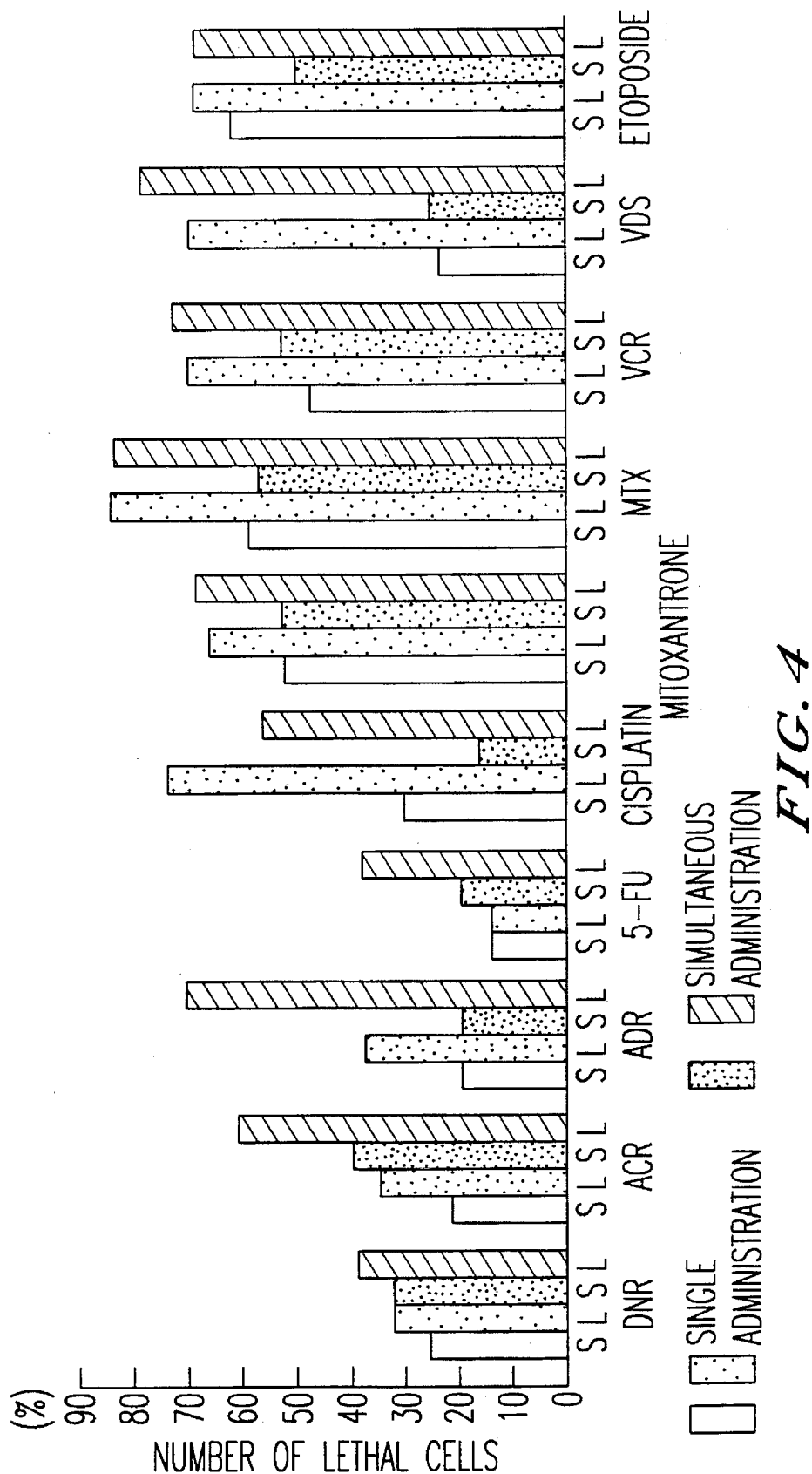
FIG. 4 is a graph which shows the results of another test for confirming an antitumor activity enhancing effect.

As apparent from FIG. 4, with respect to DNR, ACR and 5-FU, their antitumor activity was enhanced by the combined use with 4-piperidino-piperidine in both concentrations. With respect to ADR and VDS, their antitumor activity was enhanced by the combination use with 4-piperidino-piperidine in the concentration of 0.05 μg/ml.

EXAMPLE 10

The procedure of Example 9 was repeated by using human myeloblastic leukemia cells (K-562) in place of the T-ALL cells. The results are shown in FIG. 5.

Figure 5:
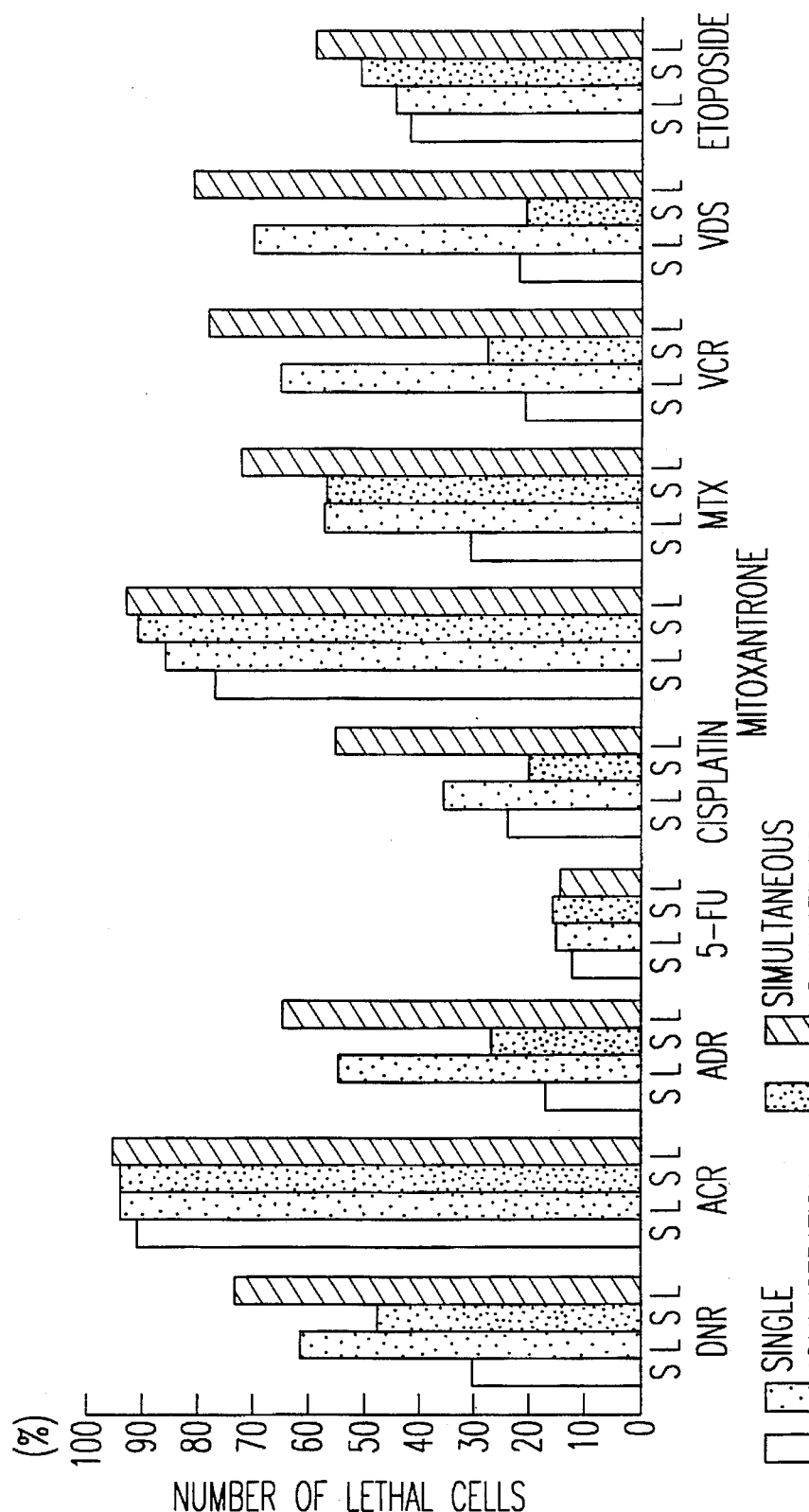
FIG. 5 is a graph which shows the results of a still another test for confirming an antitumor activity enhancing effect.

As will be understood from FIG. 5, the antitumor activity of DNR, ADR, cisplatin, mitoxantrone, MTX, VCR, VDS, and etoposide were all enhanced by the combined use with 4-piperidino-piperidine.

4-Piperidino-piperidine, which is the effective component of the medicine for the treatment of tumor according to the present invention, does not have tumor cell killing effect per se. However, they suppress propagation of tumor cells, dissolve resistance of other antitumor drugs, and enhance the antitumor activity of other antitumor drugs. Therefore, the medicine according to the present invention can be used singly in the treatment of tumor, and can also be used in combination with other antitumor drugs to improve their inherent antitumor activity. Thus, the dose of the other antitumor drugs can be reduced, which in turn minimizes adverse side effects. Accordingly, antitumor drugs which have conventionally been difficult to be put into practical use due to their severe adverse side effects can be clinically used when the medicine of the present invention is used in combination therewith.

What is claimed is:
1. A medicine for the treatment of a tumor sensitive to treatment with the composition below, comprising an enhanced composition of effective amounts of 4-piperidino-piperidine or a physiologically acceptable salt thereof, and one or more antitumor components selected from the group consisting of 5-fluorouracil, methotrexate, adriamycin, cisplatin, vincristine, vindesine, aclacinomycin, daunomycin, mitoxantrone and etoposide.

2. The medicine according to claim 1, further comprising a medicinally acceptable carrier.

3. The medicine according to claim 1, wherein the antitumor component is cisplatin.

4. A method for treating tumors sensitive to treatment with the composition below, comprising administering to said patient an effective amount of an enhanced composition comprising effective amounts of 4-piperidino-piperidine or a physiologically acceptable salt thereof, and one or more antitumor components selected from the group consisting of 5-fluorouracil, methotrexate, adriamycin, cisplatin, vincristine, vindesine, aclacinomycin, daunomycin, mitoxantrone and etoposide.

5. The method according to claim 4, wherein said composition additionally comprises a medicinally acceptable carrier.

6. The method according to claim 4, wherein the antitumor component is cisplatin.

* * * * *